United States Patent
Marsh et al.

(10) Patent No.: US 11,980,677 B2
(45) Date of Patent: *May 14, 2024

(54) WET WIPES WITH A CELLULOSIC SUBSTRATE AND GENTLE LOTION

(71) Applicant: The Procter & Gamble Company, Cincinnati, OH (US)

(72) Inventors: Randall Glenn Marsh, Hamilton, OH (US); Amber Grace Teufel, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/743,529

(22) Filed: May 13, 2022

(65) Prior Publication Data

US 2022/0370302 A1    Nov. 24, 2022

Related U.S. Application Data

(60) Provisional application No. 63/188,493, filed on May 14, 2021.

(51) Int. Cl.
| | | |
|---|---|---|
| *A61K 8/00* | (2006.01) | |
| *A47K 10/32* | (2006.01) | |
| *A61G 19/00* | (2006.01) | |
| *A61K 8/02* | (2006.01) | |
| *A61K 8/37* | (2006.01) | |
| *A61K 8/73* | (2006.01) | |
| *A61K 31/235* | (2006.01) | |
| *A61K 31/6615* | (2006.01) | |

(Continued)

(52) U.S. Cl.
CPC ............ *A61K 8/0208* (2013.01); *A61K 8/027* (2013.01); *A61K 31/235* (2013.01); *A61K 31/6615* (2013.01); *A47K 2010/3266* (2013.01); *D04H 1/4258* (2013.01)

(58) Field of Classification Search
None
See application file for complete search history.

(56) References Cited

U.S. PATENT DOCUMENTS

| 6,258,368 B1 | 7/2001 | Beerse et al. |
| 2007/0141127 A1 | 6/2007 | Casas-sanchez et al. |

(Continued)

FOREIGN PATENT DOCUMENTS

| JP | 2009263439 A | 11/2009 |
| JP | 2015110550 A | 6/2015 |

(Continued)

OTHER PUBLICATIONS

WO-013697A1—Google English Translation (Year: 2000).*

(Continued)

*Primary Examiner* — Kyung S Chang
(74) *Attorney, Agent, or Firm* — Daniel S. Albrecht

(57) ABSTRACT

A wet wipe with a substrate having cellulosic fibers and a lotion is provided. The lotion may have between about 96.0% and about 99.5%, by weight of the lotion, of water. The lotion may have a preservative system having benzoic acid and/or a salt thereof, succinic acid and/or a salt thereof, and phytic acid and/or a salt thereof. The lotion may also have a pH buffering system and a pH of about 3.5 to about 5.

20 Claims, 4 Drawing Sheets

(51) Int. Cl.
*A61Q 19/10* (2006.01)
*D04H 1/4258* (2012.01)

(56) References Cited

U.S. PATENT DOCUMENTS

| | | |
|---|---|---|
| 2017/0137366 A1 | 5/2017 | Schuch et al. |
| 2019/0024027 A1 | 1/2019 | Dowdle |
| 2019/0247283 A1 | 8/2019 | Marsh et al. |
| 2019/0247291 A1 | 8/2019 | Marsh et al. |

FOREIGN PATENT DOCUMENTS

| | | | | |
|---|---|---|---|---|
| WO | WO-013697 A1 * | 3/2000 | ........... | A23L 3/3472 |
| WO | 2006087569 A2 | 8/2006 | | |
| WO | 2018033406 A1 | 2/2018 | | |

OTHER PUBLICATIONS

Extended European Search Report and Search Opinion; Application No. 22173156.5; dated Feb. 2, 2023; 12 pages.
All Office Actions; U.S. Appl. No. 17/743,537, filed May 13, 2022.
Unpublished U.S. Appl. No. 17/743,537, filed May 13, 2022, to Randall Glenn Marsh et. al.
Mana Okasaka et al."Evaluation of anionic surfactants effects on theskin barrier function based on skin permeability", Pharmaceutical Development and Technology, vol. 24, No. 1, 2019, pp. 99-104.

* cited by examiner

WET WIPES WITH A CELLULOSIC SUBSTRATE AND GENTLE LOTION

CROSS REFERENCE TO RELATED APPLICATIONS

This application claims the benefit, under 35 U.S.C. 119(e), of U.S. Provisional Application No. 63/188,493, filed on May 14, 2021, which is incorporated by reference herein in its entirety.

FIELD

The present disclosure is directed to wet wipes comprising a substrate and a lotion, wherein the substrate comprises cellulosic fibers and the lotion inhibits and/or is resistant to bacteria, mold, and/or yeast growth. The present disclosure is also directed to wet wipes comprising a substrate and a lotion, wherein the lotion comprises a preservative system comprising benzoic acid and/or a salt thereof, succinic acid and/or a salt thereof, and phytic acid and/or a salt thereof.

BACKGROUND

Wet wipes are typically constructed from porous or absorbent sheets of substrate saturated with a lotion and are sold and stored in an air-tight container or wrapper to prevent, or at least inhibit, the sheets from drying out. Wet wipes are made for a variety of uses, including general household cleansing tasks and cleansing of human skin. A major proportion of the wipes intended for the cleansing of human skin are wet wipes which are designed for use with infants and young children. The wipes are particularly used by parents during the changing of babies to clear away fecal or urine residues in the peri-anal region before applying a fresh diaper. It is desirable for wet wipes to be effective at cleaning while at the same time being very gentle and mild on the skin of the baby, because the skin of the baby around the genitals and anus may become very sensitive or rash-prone after extended contact with urine and fecal matter.

One way to formulate a gentle and mild lotion for a wet wipe is to increase the water content of the lotion. Increasing the water content of the lotion has the added benefit of decreasing the amount of chemicals applied to the skin. However, the higher the water content of a lotion, the more difficult it may be to meet preservative system efficacy requirements for microbial growth, as water itself does not inhibit or prevent microbial growth.

Dispersion of the components of the preservative system in a lotion with a high water content often requires the use of chemical surfactants, such as emulsifiers. The use of chemical surfactants may not be desired by consumers, especially in the context of baby wet wipes, because consumers perceive chemicals as being harsh on the skin. Many chemical surfactants may also have an inherent odor based on their chemistry and how they were manufactured. This odor may be exacerbated if the lotion has a low pH, for example below 4.0. When assembled together into a lotion, even a fairly small number of raw materials, such as surfactants, can result in a final formulation that has a characteristic odor that may be noticeable and undesirable to consumers.

Components of a lotion with a high water content, especially those without emulsifiers, may also be more readily available to participate in reactions with the wet wipe substrate. Such reactions may reduce the ability of the components involved to function as part of the preservative system, thus reducing the effectiveness of the preservative system to inhibit or prevent microbial growth. As such, wet wipe lotions and substrates should be improved.

SUMMARY

The present disclosure solves at least some of the problems discussed above by providing wet wipes comprising a lotion with a high concentration of water. The lotion may be gentle on the skin, while inhibiting or preventing microbial growth. The wet wipes of the present disclosure may also comprise a substrate comprising cellulosic fibers. A substrate comprising cellulosic fibers may have reduced interaction with the components of the lotion preservative system, allowing for improved functioning of the preservative system.

The present disclosure provides, in part, wet wipes comprising a substrate comprising cellulosic fibers and a lotion. The lotion comprises between about 96.0% and about 99.5%, by weight of the lotion, of water. The lotion also comprises a pH buffering system and a preservative system comprising benzoic acid and/or a salt thereof, succinic acid and/or a salt thereof, and phytic acid and/or a salt thereof. The lotion has a pH of about 3.5 to about 5. A lotion comprising a preservative system comprising benzoic acid and/or a salt thereof, succinic acid and/or a salt thereof, and phytic acid and/or a salt thereof may not require a surfactant to stabilize the system, which may be consumer preferred.

The present disclosure also provides, in part, wet wipes comprising a substrate comprising 100% cellulosic fibers and a lotion. The lotion comprises between about 96.0% and about 99.5%, by weight of the lotion, of water. The lotion also comprises a pH buffering system and a preservative system comprising benzoic acid and/or a salt thereof, succinic acid and/or a salt thereof, and phytic acid and/or a salt thereof. The lotion has a pH of about 3.5 to about 5.

The present disclosure also provides, in part, wet wipes comprising a substrate comprising 100% cellulosic fibers and a lotion. The lotion comprises between about 96.0% and about 99.5%, by weight of the lotion, of water. The lotion also comprises a pH buffering system and a preservative system comprising benzoic acid and/or a salt thereof, succinic acid and/or a salt thereof, and phytic acid and/or a salt thereof. The lotion has a pH of about 3.6 to about 4.4. The lotion is free of fatty acid-containing materials. The wet wipes have a Benzoate Retention Factor at 1 month of between about 45% and about 99%, according to the Benzoate Retention Test Method disclosed herein. The lotion has a Bacterial Log Reduction Factor of greater than or equal to 3 at day 28, according to the Microbiological Susceptibility Test Method described herein, and a Yeast and Mold Log Reduction Factor of greater than or equal to 2 at day 28, according to the Microbiological Susceptibility Test Method described herein.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Figure 1:
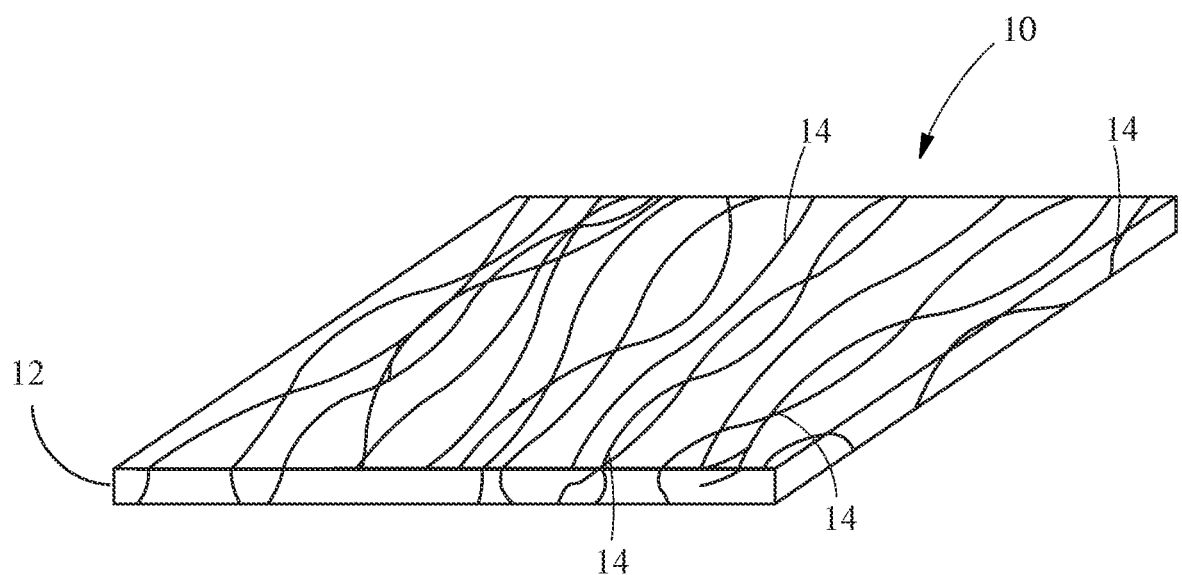
FIG. 1 is a schematic illustration of a wet wipe substrate comprising one layer.

Various non-limiting forms of the present disclosure will now be described to provide an overall understanding of the principles of the structure, function, manufacture, and use of the wet wipes with a cellulosic substrate and gentle lotion disclosed herein. One or more examples of these non-limiting forms are illustrated in the accompanying drawings. Those of ordinary skill in the art will understand that the wet wipes with a cellulosic substrate and gentle lotion described herein and illustrated in the accompanying drawings are non-limiting example forms. The features illustrated or described in connection with one non-limiting form may be combined with the features of other non-limiting forms. Such modifications and variations are intended to be included within the scope of the present disclosure.

As used herein, the terms "Devoid of," "free of," and the like, mean that the wet wipe, lotion, and/or substrate does not have more than trace amounts or background levels of a given material, ingredient, or characteristic following these qualifiers, or the material or ingredient was not added to the wet wipe, lotion, and/or substrate intentionally. In some instances, "devoid of" and "free of" can mean there is no measurable amount of the material or ingredient.

Lotion

The aqueous portion of a wet wipe, herein referred to as a lotion, may comprise various chemical constituents that carry out functions such as cleaning, buffering, and preservation, as will be discussed in detail herein. The lotion may assist in the cleaning function of a wet wipe by, for example, solubilizing and clearing away fecal and/or urine residue from the skin of a baby.

The wet wipes disclosed herein comprise a lotion. The lotion may comprise from about 96% water to about 99.5% water, from about 97% water to about 99.1% water, or from about 98.2% water to about 98.9% water, by weight of the lotion, specifically reciting every 0.1% increment within these ranges and any ranges formed therein or thereby, according to the Water Content Method disclosed herein. A wet wipe lotion comprising water within the above-specified ranges may be gentle on the skin, especially when the wet wipe is employed to cleanse delicate areas of the body.

The lotions described herein may be made by the conventional processes described in the art. Alternatively, the lotions and wipes may be made according to U.S. Pat. No. 7,365,030 entitled "Process for making a wet wipe using a concentrated emulsion" by Sylvie Chamba et al.

Lotion Preservative System

The lotions of the present disclosure may comprise a preservative system. A preservative system may be understood to be a synthetic or natural compound, or a combination of compounds, that may be effective in reducing or preventing the growth of microorganisms, thus enabling a longer shelf life for a package of wet wipes (opened or not opened). The preservative system may also create an environment that reduces or inhibits growth of microorganisms when the lotion is transferred to the skin during the wiping process. The preservative system may be especially useful when a wet wipe lotion comprises a high concentration of water, such as, for example, greater than about 96% of the lotion formulation.

The spectrum of activity of the preservative systems disclosed herein may include bacteria, molds, and/or yeast. One of, or every, such microorganism may be killed by a preservative system of the present disclosure. Another mode of action of the preservative systems may be the reduction of the growth rate of the microorganisms without active killing.

The preservative systems of the present disclosure may comprise a natural compound or compounds. Natural compounds may be compounds derived from plants and/or animals, or from natural processes of plants and/or animals, such as fermentation, for example. Natural compounds may be, or may be perceived by consumers to be, gentler on the skin of a user as compared to man-made compounds. Natural compounds may comprise compounds derived from plants and/or animals without any post-harvest treatment steps, as well as those receiving post-harvest treatment steps, such as neutralization reactions to form a salt, for example. The lotion of the present disclosure may comprise a preservative system comprising a natural preservative or preservatives. The lotion may comprise a 100% plant-based preservative system. The preservative system may consist essentially of natural compounds. The preservative system may consist of natural compounds.

The lotion preservative systems of the present disclosure may comprise benzoic acid and/or a salt thereof. Benzoic acid is a carboxylic acid that occurs naturally in many plant and animal species. The lotions of the present disclosure may comprise at least 0.1%, at least 0.14%, at least 0.17%, or from about 0.1% to about 0.6%, from about 0.1% to about 0.4%, from about 0.1% to about 0.3%, from about 0.1% to about 0.25%, from about 0.14% to about 0.4%, from about 0.14% to about 0.3%, from about 0.17% to about 0.3%, or from about 0.17% to about 0.25% of benzoic acid, by weight of the lotion, in the form of benzoic acid and/or a salt thereof, specifically reciting every 0.01% increment within these ranges and any ranges formed therein or thereby. The lotion may comprise sodium benzoate. The lotion may comprise benzoic acid and sodium benzoate.

The lotion preservative systems of the present disclosure may comprise succinic acid and/or a salt thereof. Succinic acid is a dicarboxylic acid that is found in many plant and animal sources, and may also be synthesized through fermentation by certain microorganisms. Succinic acid is used in the food industry as an acidity regulator and a flavoring agent. Succinic acid has unexpectedly been found to provide hostility against microorganisms in lotions with high a high water content. The lotions of the present disclosure may comprise at least 0.15%, at least 0.2%, at least 0.25%, from about 0.15% to about 0.6%, or from about 0.1% to about 0.4%, from about 0.1% to about 0.3%, from about 0.2% to about 0.6%, from about 0.2% to about 0.45%, from about 0.2% to about 0.4%, from about 0.25% to about 0.4%, or from about 0.25% to about 0.35% of succinic acid, by weight of the lotion, in the form of succinic acid and/or a salt thereof, specifically reciting every 0.01% increment within these ranges and any ranges formed therein or thereby. The lotion may comprise sodium succinate. The lotion may comprise succinic acid and sodium succinate.

The lotion preservative systems of the present disclosure may comprise phytic acid and/or a salt thereof. Phytic acid is an organic acid that occurs naturally, for example, in many legumes, grains, and the bran of cereals. The lotions of the present disclosure may comprise at least 0.02%, at least 0.04%, at least 0.06%, or from about 0.02% to about 0.2%, from about 0.02% to about 0.15%, from about 0.02% to about 0.1%, from about 0.04% to about 0.2%, from about 0.04% to about 0.15%, from about 0.04% to about 0.1%, from about 0.06% to about 0.1%, or from about 0.06% to about 0.08% of phytic acid, by weight of the lotion, in the form of phytic acid and/or a salt thereof, specifically reciting every 0.01% increment within these ranges and any ranges formed therein or thereby. The lotion may comprise sodium phytate. The lotion may comprise phytic acid and sodium phytate.

The lotions of the present disclosure may be free of surfactants. The selection of compounds making up the preservative system of the lotions described herein may be effective in reducing or inhibiting the growth of microorganisms, such as bacteria, yeast, and mold, without the need for surfactants to stabilize the preservative system components in the aqueous medium of the lotion. Many surfactants used in wet wipe applications comprise fatty acids and/or are derived from plant-based oils, such as sorbitan caprylate, polysorbate-20, and PEG-40 hydrogenated castor oil. Such surfactants may contribute a fatty odor to the lotion. This fatty odor may be exacerbated if the lotion has a low pH, example below 4.0, due to acid-catalyzed hydrolysis of fatty esters and resulting in generation of free fatty acids over time. Fatty acids may have an odor that is detectable at very low concentrations to the human nose. When assembled together into a lotion, even a small amount of fatty acid-containing materials can result in a final formulation that has a characteristic odor that may be noticeable and undesirable to consumers. The lotions of the present disclosure may be free of fatty acid-containing compounds.

Lotion Buffering System

The lotions of the present disclosure may comprise a pH buffering system. The pH buffering system may be present at from about 0.3% to about 1%, from about 0.4% to about 1%, from about 0.5% to about 0.85%, or from about 0.55% to about 0.75%, by weight of the lotion, specifically reciting every 0.01% increment within these ranges and any ranges formed therein or thereby. The pH buffering system may help prevent or reduce the growth of, or kill, bacteria, mold, and/or yeast by, for example, maintaining a pH of the lotion that is hostile to the growth of bacteria, mold, and/or yeast, or by maintaining a pH that makes the bacteria, mold, and/or yeast more susceptible to the preservative system. The pH buffering system may be a citrate-citric acid buffering system at a pH of less than 5. The pH buffering system may be a citrate-citric acid buffering system at a pH of less than 4. The pH buffering system may be a sodium citrate-citric acid buffering system at a pH of less than 5. The pH buffering system may be a sodium citrate-citric acid buffering system at a pH of less than 4. The pH buffering system may comprise sodium citrate dihydrate and citric acid anhydrous. The lotions of the present disclosure may have a pH from about 3.4 to about 6, from about 3.5 to about 5, from about 3.6 to about 4.8, from about 3.6 to about 4.4, from about 3.6 to about 4.2, or from about 3.8 to about 4.2, specifically reciting every 0.1% increment within these ranges and any ranges formed therein or thereby.

The Equivalence Value of a lotion may be an indication of the lotion's resistance to an increase in pH. A lotion having a higher Equivalence Value may be desired because it may help to protect a baby's skin against irritation caused by feces and urine residue that remains after cleaning. The proteases in feces that may damage the skin can start to become active around pH 5 and can reach peak activity between pH 7 to 8. Urea in urine may be converted to ammonia by bacteria on the skin, elevating the pH and making the fecal proteases more active. By depositing a lotion with a higher Equivalence Value on the skin, an acidic buffer may be created that resists the rise in pH that may otherwise occur over time and/or when trace amounts of feces and urine are present. By resisting the rise in pH, a lotion with a higher Equivalence Value may protect the skin from damage caused by fecal proteases and reduce the likelihood that rash will occur between diaper changes. The lotions of the present disclosure may have an Equivalence Value from about 25 to about 100, from about 30 to about 95, from about 55 to about 90, from about 65 to about 90, from about 60 to about 80, from about 62 to about 75, or from about 65 to about 70, specifically reciting every 1.0 unit increment within these ranges and any ranges formed therein or thereby, according to the Buffering Capacity Test Method described herein.

Lotion Optional Ingredients

The lotions of the present disclosure may include various optional ingredients, such as emollients, opacifying agents, film-formers, soothing agents, skin protectants, medically active ingredients, healing actives, and the like, such as described in U.S. Pat. Nos. 7,666,827; 7,005,557; 8,221,774.

The lotions of the present disclosure may comprise an emollient or emollients. Emollients may (1) hydrate soil residues (for example, fecal residues or dried urine residues or menses residues), thus enhancing their removal from the skin, (2) hydrate the skin, thus reducing its dryness and irritation, (3) protect the skin from later irritation (for example, caused by the friction of an absorbent article) as the emollient is deposited onto the skin and remains at its surface as a thin protective layer, and/or (4) provide a desired sensory feel to the lotion and/or the skin.

The lotions of the present disclosure may comprise one or more rheology modifiers. A rheology modifier may help to stabilize the lotion by, for example, reducing or preventing coalescence of droplets of the hydrophobic materials in the composition. Non-limiting examples of rheology modifiers include, but are not limited to, hydrocolloids, including natural gums, such as xanthan gum. The lotions of the present disclosure may comprise from about 0.01% to about 0.1%, from about 0.03% to about 0.08%, from about 0.05% to about 0.07%, or about 0.06% of a rheology modifier, by weight of the lotion, specifically reciting every 0.01% increment within these ranges and every range formed therein or thereby.

The lotions of the present disclosure may comprise a fragrance and/or a perfume. The fragrance and/or perfume may be a natural compound or compounds. The wet wipe of the present disclosure may be devoid of fragrance and/or perfume.

The lotions of the present disclosure may comprise natural plant extracts. The natural plant extracts may be selected from grape (*Vitis vinifera*) seed extract, *Camellia sinensis* (tea) leaf extract, *Hamamelis virginiana* leaf extract, *Calendula officinalis* flower extract, and combinations thereof.

The lotions of the present disclosure may comprise an odor reducing composition. The odor reducing composition may be a naturally derived odor reducing composition. The naturally derived odor reducing composition may manage odors inherent to the raw materials used in the manufacture of the wet wipe and/or manage odors associated with wet wipe (e.g., urine, feces, etc.). The naturally derived odor reducing composition may include plant extracts. Exemplary plant extracts may include magnolia extract and/or marigold extract, such as Extrapone® Marigold GW and Extrapone® Magnolia GW from Symrise. The naturally derived odor reducing composition may be substantially scent-free.

The lotions of the present disclosure may be incorporated onto a substrate at a load of about 200% to about 600%, from about 300% to about 500%, or from about 325% to about 460%, by weight of the substrate, specifically reciting every 1% increment within these ranges and every range formed therein or thereby.

Wet Wipe Substrates

Figure 2:
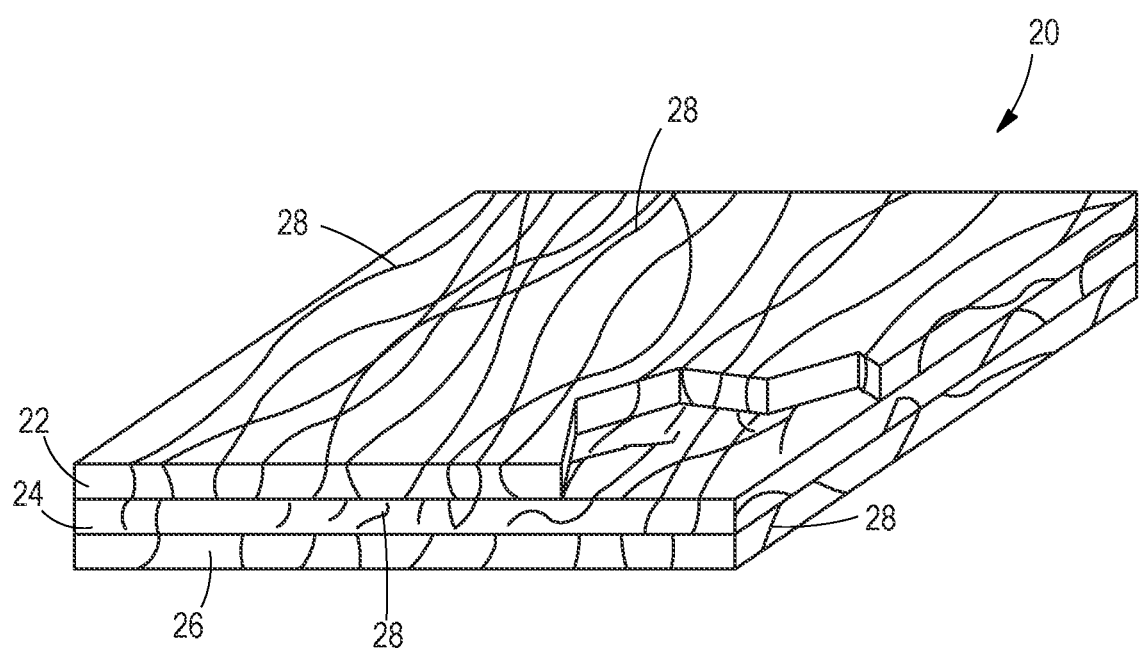
FIG. 2 is a schematic illustration of a wet wipe substrate comprising multiple layers.

The lotions of the present disclosure may be loaded onto a substrate to form a wet wipe. The substrate may be homogenous or may be layered. If layered, the substrate may comprise at least two, at least three, at least four, or at least five layers. Referring to FIG. 1, the substrate 10 may be formed of one layer 12 of a web of fibers 14. Referring to FIG. 2, the substrate 20 may be formed of more than one layer of webs of fibers 28. For example, the substrate 20 may be formed of a first layer 22 of a web of fibers 28, a second layer 24 of a web of fibers 28, and a third layer 26 of a web of fibers 28. The one or more layers of webs of fibers may comprise a nonwoven web of materials comprising continuous fibers, coextruded fibers, non-continuous fibers, and/or combinations thereof. Nonwoven web materials may comprise cellulosic fibers, modified cellulosic fibers, synthetic fibers, mixtures of cellulosic and/or modified cellulosic fibers with synthetic fibers, and/or combinations thereof. The fibers comprising the nonwoven web materials may be processed to be suitably soft-feeling against the skin.

The nonwoven web materials may include, consist essentially of, or consist entirely of cellulosic fibers. Non-limiting examples of cellulosic fibers include wood pulp, typical northern softwood Kraft, typical southern softwood Kraft, typical CTMP, typical deinked, corn pulp, acacia, eucalyptus, aspen, reed pulp, birch, maple, radiata pine, albardine, esparto, wheat, rice, corn, sugar cane, papyrus, jute, reed, sabia, raphia, bamboo, sidal, kenaf, abaca, cotton, flax, hemp, jute, modified natural cellulosic fibers such as, for example, rayon (including viscose, lyocell, MODAL (a product of Lenzing AG, Lenzing, Austria) and cuprammonium rayon), and combinations thereof. Cellulosic fibers may be consumer-preferred to appeal to a desire for natural and/or environmentally friendly products. The cellulosic fibers may be treated or otherwise modified mechanically and/or chemically to provide desired characteristics, or may be in a form that is generally similar to the form in which they may be found in nature. Mechanical and/or chemical manipulation of natural fibers does not exclude them from what are considered natural fibers with respect to the present disclosure.

The nonwoven web materials may comprise synthetic fibers. Non-limiting examples of synthetic fibers include polyesters (e.g., polyethylene terephthalate), polyolefins, polypropylenes, polyethylenes, polyethers, polyamides, polyesteramides, polyvinylalcohols, polyhydroxyalkanoates, polysaccharides, and combinations thereof. The polyester may comprise less than 100 ppm antimony, or the polyester may be devoid of antimony. Further, the synthetic fibers may be a single component (i.e., single synthetic material or mixture makes up entire fiber), bi-component (i.e., the fiber is divided into regions, the regions including two or more different synthetic materials or mixtures thereof and may include co-extruded fibers and core and sheath fibers) and combinations thereof. Bi-component fibers may be used as a component fiber of the structure, and/or they may be present to act as a binder for the other fibers present in the fibrous structure. Any or all of the synthetic fibers may be treated before, during, or after manufacture to change any desired properties of the fibers. The substrate may comprise hydrophilic fibers, hydrophobic fibers, or a combination thereof.

The wet wipe substrate may comprise between about 30% and about 100%, between about 50% and about 100%, or between about 65% and 100%, by weight of the substrate of cellulosic fibers, specifically reciting each 1% increment within these ranges and every range formed therein or thereby. The substrate may comprise about 50% cellulosic fibers and about 50% synthetic fibers, by weight of the substrate. The substrate may comprise about 30% cellulosic fibers and about 70% synthetic fibers, by weight of the substrate. The substrate may comprise about 100% cellulosic fibers, such as a mixture of about 50% viscose and about 50% lyocell, by weight of the substrate. The substrate may comprise about 100% cellulosic fibers, such as a mixture of about 85% lyocell and about 15% cotton, by weight of the substrate. The substrate may comprise about 100% cellulosic fibers, wherein the cellulosic fibers comprise between about 10% to about 70% viscose, by weight of the substrate. The substrate may be devoid of polyesters, polyamides, and/or polyolefins.

It may be desirable that the substrate, or at least one or more layers of the substrate, comprises a particular combinations of fibers to provide desired characteristics. For example, it may be desirable to have fibers of certain lengths, widths, coarseness, or other characteristics combined in certain layers, or separate from each other. The fibers may be of virtually any size and may have an average length from about 1 mm to about 60 mm, specifically reciting each 1 mm increment within the range and every range formed therein. Average fiber length refers to the length of the individual fibers if straightened out. The fibers may have an average fiber width of greater than about 5 micrometers. The fibers may have an average fiber width of from about 5 micrometers to about 50 micrometers, specifically reciting each 1 micrometer increment within the range and every range formed therein. The fibers may have a coarseness of greater than about 5 mg/100 m. The fibers may have a coarseness of from about 5 mg/100 m to about 75 mg/100 m, specifically reciting each 1 mg/100 m increment within the range and every range formed therein.

The fibers may be circular in cross-section, dog-bone shape, delta (i.e., triangular cross section), trilobal, ribbon, or other shapes typically produced as staple fibers. Likewise, the fibers may be conjugate fibers such as bicomponent fibers. The fibers may be crimped and may have a finish, such as a lubricant, applied.

The materials comprising the substrate may be treated to improve the softness and texture thereof. The substrate may be subjected to various treatments, such as physical treatment, hydro-molding, hydro-embossing, hydro-entangling, ring rolling, as described in U.S. Pat. No. 5,143,679; structural elongation, as described in U.S. Pat. No. 5,518,801; consolidation, as described in U.S. Pat. Nos. 5,914,084; 6,114,263; 6,129,801 and 6,383,431; stretch aperturing, as described in U.S. Pat. Nos. 5,628,097; 5,658,639; and 5,916,661; differential elongation, as described in U.S. Pat. No. 7,037,569, other solid state formation technologies as described in U.S. Pat. Nos. 7,553,532; 7,410,683; zone activation, and the like; chemical treatment, such as rendering part or all of the substrate hydrophobic and/or hydrophilic, and the like; thermal treatment, such as thermal-embossing, softening of fibers by heating, thermal bonding and the like; and combinations thereof.

Figure 3:
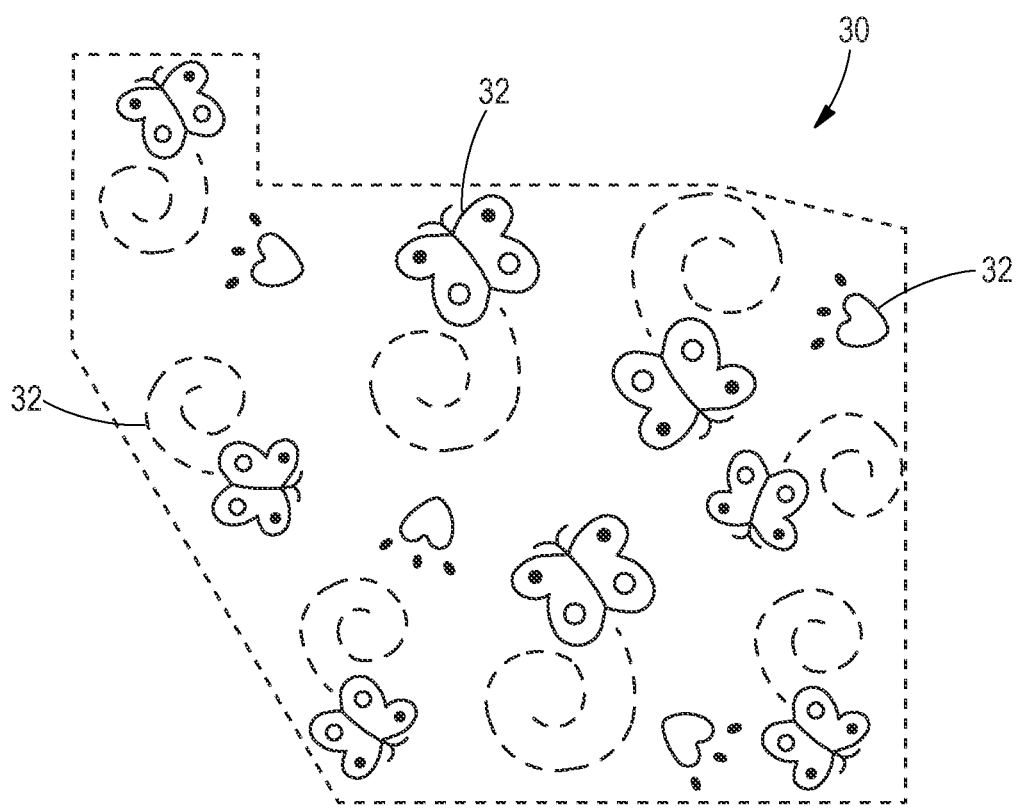
FIG. 3 is a schematic illustration of a wet wipe substrate comprising a plurality of texture elements that form a pattern.

Without wishing to be bound by theory, it is believed that a textured substrate may further enable the ease of removal of soils by improving the ability to grip or otherwise lift the soils from the surface during cleansing. Any one of a number of texture elements may be useful in improving the ability to grip or otherwise lift the soil from the surface during cleansing, such as continuous hydro-molded elements, hollow molded element, solid molded elements, circles, squares, rectangles, ovals, ellipses, irregular circles, swirls, curly cues, cross hatches, pebbles, lined circles, linked irregular circles, half circles, wavy lines, bubble lines, puzzles, leaves, outlined leaves, plates, connected circles, changing curves, dots, honeycombs, and the like, and combinations thereof. The texture elements may be hollow elements. The texture elements may be connected to each other. The texture elements may overlap each other. The texture elements may form a pattern. Referring to FIG. 3, the substrate 30 may comprise a plurality of texture elements 32 that form a pattern in and/or on the substrate 30.

The substrate may have a basis weight between about 15 grams/m$^2$ (gsm) and about 100 gsm, between about 30 gsm and about 95 gsm, between about 40 gsm and about 85 gsm, between about 45 gsm and about 75 gsm, or between about 52 gsm and about 65 gsm, specifically reciting every 1 gsm increment within the ranges and every range formed therein or thereby. Exemplary nonwoven substrates are described in U.S. Patent Publication 2012/066852 and U.S. Patent Publication U.S. 2011/244199.

The surface of the substrate may be essentially flat. The surface of the substrate may optionally contain raised and/or lowered portions. The raised and/or lowered portions may be in the form of logos, indicia, trademarks, geometric patterns, and/or images of the surfaces that the substrate is intended to clean (i.e., infant's body, face, etc.). The raised and/or lowered portions may be randomly arranged on the surface of the substrate or be in a repetitive pattern.

The substrate may be biodegradable. For example, the substrate may comprise a biodegradable material such as a polyesteramide or a high wet strength cellulose. The substrate may be dispersible in water.

The substrates described herein may have different properties on different sides of the substrate. For example, one side of the substrate may have good cleaning performance and the other side of the substrate may have good tactile sensation to the user. In another form, one side of the substrate may have an increased cleaning performance as compared to the other side of the substrate.

Non-limiting examples of processes for making webs of fibers of the substrate described herein include known wet-laid papermaking processes, air-laid papermaking processes including carded and/or spunlaced processes. Such processes typically include steps of preparing a fiber composition in the form of a suspension in a medium, either wet, more specifically aqueous medium, or dry, more specifically gaseous, i.e., with air as a medium. The aqueous medium used for wet-laid processes is oftentimes referred to as a fiber slurry. The fibrous slurry is then used to deposit a plurality of fibers onto a forming wire or belt such that an embryonic web of fibers is formed, after which drying and/or bonding the fibers together results in a web of fibers. Further processing the web of fibers may be carried out such that a finished web of fibers is formed. For example, in typical papermaking processes, the finished web of fibers is the fibrous structure that is wound on the reel at the end of papermaking, and may subsequently be converted into a finished product, e.g., a wet wipe substrate.

The web of fibers of the substrates described herein may be a co-formed fibrous structure. "Co-formed fibrous structure," as used herein, means that the fibrous structure comprises a mixture of at least two different materials, wherein at least one of the materials comprises a filament, such as a polypropylene filament, and at least one other material different from the first material, comprises a solid additive, such as a fiber and/or a particulate. In one example, a co-formed fibrous structure comprises solid additives—such as fibers (for example, wood pulp fibers) and/or absorbent gel materials and/or filler particles and/or particulate spot bonding powders and/or clays—and filaments—such as polypropylene filaments. "Solid additive" as used herein means a fiber and/or a particulate. "Particulate" as used herein means a granular substance or powder. "Fiber" and/or "Filament" as used herein means an elongate particulate having an apparent length greatly exceeding its apparent width, i.e., a length to diameter ratio of at least about 10. For purposes of the present disclosure, a "fiber" is an elongate particulate as described above that exhibits a length of less than 5.08 cm (2 in.) and a "filament" is an elongate particulate as described above that exhibits a length of greater than or equal to 5.08 cm (2 in.).

Figure 4:
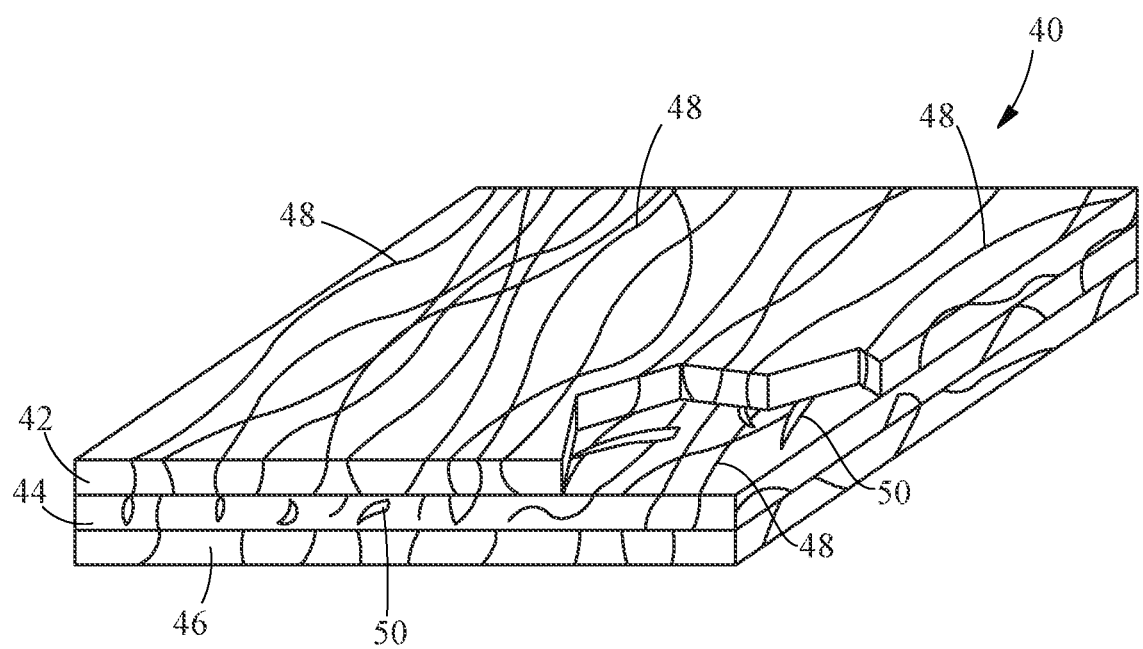
FIG. 4 is a schematic illustration of a co-formed wet wipe substrate.

Referring to FIG. 4, the substrate 40 may be a co-formed layered fibrous structure. The co-formed layered fibrous structure may comprise a first layer 44 comprising a plurality of filaments 48, such as polypropylene filaments, and a plurality of solid additives 50, such as wood pulp fibers, for example. The co-formed layered fibrous structure 40 may further comprise a second layer 42 and a third layer 46, each comprising a plurality of filaments 48, such as polypropylene filaments, for example. The first layer 44 may be disposed between the second layer 42 and the third layer 46. In a form, the first, second, and third layers may be sharply defined zones of concentration of the filaments and/or solid additives. The plurality of filaments of the second and third layers may be deposited directly onto a surface of the first layer to form the co-formed layered fibrous structure. In another form, the first layer may form an outward-facing surface of the substrate and may be in direct contact with only one other layer.

The substrate described herein may be subjected to any post-processing operations such as embossing operations, printing operations, tuft-generating operations, thermal bonding operations, ultrasonic bonding operations, perforating operations, surface treatment operations such as application of lotions, silicones and/or other materials, folding, and/or combinations thereof.

Without being bound by theory, it is believed that different compounds present in a wipe lotion may interact to different degrees with the various kinds of nonwoven fibers that are present in a wipe substrate, once the wipe lotion is applied to the substrate. Different kinds of interactions may occur based on the physical and chemical properties of the lotion compound and of the nonwoven fibers. These interactions may lead to adsorption of the lotion compound to the surface of the fiber or to absorption of the lotion compound into the structure of the fiber.

Hansen's solubility parameters are a way of predicting if one material may tend to interact with, and potentially absorb into or adsorb to, another material. Each molecule is given three Hansen parameters, one for the dispersion forces between molecules, one for the dipolar intermolecular force between molecules, and one for the hydrogen bonding between molecules. These parameters serve as coordinates for a point in three dimensions known as the Hansen space. The nearer two molecules are in this three-dimensional space, the more compatible they are, the more likely they are to interact, and the greater the potential for them to absorb into or adsorb to each other.

In the case of polyester fibers, certain organic acids, such as benzoic acid, share physical and chemical similarities to polyester that may cause them to have a fairly similar Hansen space. This means that, over time, while a wipe lotion is in contact with a wipe substrate comprising polyester fibers, certain organic acids, such as benzoic acid, and/or a salt thereof, may interact with (absorb into or adsorb onto) the polyester fibers, reducing their concentration in the wipe lotion and making them unavailable to participate in preservative system efficacy. One way to measure the affinity of substrate components to interact with benzoic acid and/or benzoate in a lotion composition is to measure the retention of benzoic acid and/or salt thereof in the lotion after exposure to a substrate material for a period of time, known herein as the Benzoate Retention Factor. Such a measurement may be made according to the Benzoate Retention Test Method disclosed herein. The wet wipes of the present disclosure may have a Benzoate Retention Factor at 1 month of between about 45% and about 99%, between about 50% and about 99%, between 55% and about 99%, or between about 60% and about 99%, specifically reciting every 1% increment within the ranges and every range formed therein or thereby, according to the Benzoate Retention Test Method disclosed herein. The wet wipes of the present disclosure may have a Benzoate Retention Factor at 3 months of between about 40% and about 99%, between about 45% and about 99%, between about 50% and about 99%, or between about 55% and about 99%, specifically reciting every 1% increment within the ranges and every range formed therein or thereby, according to the Benzoate Retention Test Method disclosed herein.

In addition to measuring the retention of benzoic acid and/or a salt thereof in the lotion, the efficacy of the lotion preservative system to inhibit and/or reduce microbial growth may be tested according to the Microbiological Susceptibility Test (MST) Method disclosed herein. The wet wipes of the present disclosure may have a Bacterial Log Reduction Factor of greater than or equal to 3 at day 28, according to the Microbiological Susceptibility Test Method disclosed herein. The wet wipes of the present disclosure may have a Yeast and Mold Log Reduction Factor of greater than or equal to 2 at day 28, according to the Microbiological Susceptibility Test Method disclosed herein. The wet wipes of the present disclosure may have an overall MST score of "Pass", according to the Microbiological Susceptibility Test Method disclosed herein. An overall MST score of "Pass" indicates that the preservative system of a lotion is robust and capable of preserving wet wipes over shelf life.

EXAMPLES AND DATA

The following examples and comparative examples are provided to help illustrate the lotions and substrates described herein. The exemplified lotions may be prepared by conventional formulation and mixing techniques. It will be appreciated that other modifications of the lotions described herein within the skill of those in the formulation art may be undertaken. All parts, percentages, and ratios herein are by weight unless otherwise specified.

Table 1 list the ingredients comprising the lotions of Examples 1-4 and Comparative Examples 1-9.

Example 1: The wet wipe of the present disclosure described as Example 1 is a substrate comprising a 50:50 blend of viscose and lyocell in a lotion comprising 98.22% water, 0.2% sodium benzoate, 0.3% succinic acid, 0.88% citric acid (50% solution), 0.30% sodium citrate, and 0.10% phytic acid. The lotion load rate is 325% by weight of the substrate.

Example 2: The wet wipe of the present disclosure described as Example 2 is a substrate comprising a 50:50 blend of viscose and lyocell in a lotion comprising 98.22% water, 0.2% sodium benzoate, 0.3% succinic acid, 0.88% citric acid (50% solution), 0.30% sodium citrate, and 0.10% sodium phytate. The lotion load rate is 325% by weight of the substrate.

Example 3: The wet wipe of the present disclosure described as Example 3 is a substrate comprising a 50:50 blend of viscose and lyocell in a lotion comprising 98.22% water, 0.2% sodium benzoate, 0.3% succinic acid, 0.88% citric acid (50% solution), 0.30% sodium citrate, and 0.10% phytic acid. The lotion load rate is 390% by weight of the substrate.

Example 4: The wet wipe of the present disclosure described as Example 4 is a substrate comprising a 50:50 blend of viscose and lyocell in a lotion comprising 98.22% water, 0.2% sodium benzoate, 0.3% succinic acid, 0.88% citric acid (50% solution), 0.30% sodium citrate, and 0.10% sodium phytate. The lotion load rate is 390% by weight of the substrate.

Comparative Examples 1-9: The wet wipe of the present disclosure described as Comparative Examples 1-9 are commercially purchased wet wipe products containing the ingredients listed in Table 1, as disclosed on the ingredients listing of each Comparative Example product.

TABLE 1

|  | Water | Benzoic Acid | Succinic Acid | Phytic Acid | Surfactants | Other ingredients |
| --- | --- | --- | --- | --- | --- | --- |
| Example 1 | Yes | Yes | Yes | Yes | None | None |
| Example 2 | Yes | Yes | Yes | Yes | None | None |
| Example 3 | Yes | Yes | Yes | Yes | None | None |
| Example 4 | Yes | Yes | Yes | Yes | None | None |

TABLE 1-continued

| | Water | Benzoic Acid | Succinic Acid | Phytic Acid | Surfactants | Other ingredients |
|---|---|---|---|---|---|---|
| Comp. Example 1 | Yes | Yes | No | No | Polysorbate 20, Coco-betaine | Malic Acid, Fragrance, *Aloe barbadensis* Leaf Extract, Tocopheryl Acetate |
| Comp. Example 2 | Yes | Yes | No | No | Coco-betaine, Polysorbate 20, Butoxy-Peg-4 PG_amodimethicone | Glycerin, Malic Acid, Fragrance, *Aloe barbadensis* Leaf Extract, Tocopheryl Acetate, Thebromo cocao Extract, Shea Butter |
| Comp. Example 3 | Yes | Yes | No | No | Coco-glucoside, Butoxy-Peg-4 PG_amodimethicone | *aloe barbadensis* leaf juice malic acid, tocopheryl acetate |
| Comp. Example 4 | Yes | Yes | No | No | Polysorbate 20, Coco-betaine | glycerin, malic acid, fragrance, *aloe barbadensis* leaf extract, tocopheryl acetate, *Cucumis* sativus fruit extract, *Calendula Officinalis* flower extract, Camelia sinensis leaf extract |
| Comp. Example 5 | Yes | No | No | No | Coco-glucoside, Polyglyceryl-2-dipolyhydroxysterate | *Aloe barbadensis* leaf juice, *avena* sativa kernel extract, glycerin, glyceryl polyacrylate, carbomer, sodium hydroxide |
| Comp. Example 6 | Yes | Yes | No | No | None | *Aloe barbadensis* extract, *Calendula officinalis* flower extract, *Chamomila recruittia* flower extract, *Cucumis* sativus fruit extract, *Glycyrrhiza* glabra root extract, glycerin, tocopheryl acetate, tetrasodium glutamate diacetate, sodium bicarbonate |
| Comp. Example 7 | Yes | Yes | No | No | cocamidopropyl PG-dimonium chloride phosphate, | glycerin, bisabolol, *Calendula officinalis* flower extract, *Chamomilla recuttia* flower extract, simethicone, *Aloe barbadensis* leaf extract, tocopheryl acetate, *Citrus* grandis seed extract |
| Comp. Example 8 | Yes | No | No | No | None | *Citrus* grandis seed extract |
| Comp. Example 9 | Yes | Yes | No | No | myristamidopropyl PG dimonium chloride phosphate | *Aloe barbadensis* leaf juice, organic aloe vera |

Table 2 shows the Bacteria Log Reduction Value, the Yeast and Mold Log Reduction Value, and the overall MST Score of Examples 1-4 and Comparative Examples 1-9, according to the Microbiological Susceptibility Test Method described herein.

TABLE 2

|  | Bacteria Log Reduction Value (log reduction) | | | Yeast & Mold Log Reduction Value (log reduction) | | Overall MST Score |
|---|---|---|---|---|---|---|
|  | Day 2 | Day 7 | Day 28 | Day 14 | Day 28 | (pass/fail) |
| Example 1 | 4.4 | 5.2 | 5.2 | 4.2 | 4.7 | Pass |
| Example 2 | 5.2 | 5.2 | 5.2 | 4.0 | 4.7 | Pass |
| Example 3 | 5.2 | 5.2 | 5.2 | 4.7 | 4.7 | Pass |
| Example 4 | 5.2 | 5.2 | 5.2 | 4.7 | 4.7 | Pass |
| Comp. Example 1 | 4.9 | 4.9 | 4.9 | 3.3 | 4.3 | Pass |
| Comp. Example 2 | 4.9 | 4.9 | 4.9 | 3.3 | 4.3 | Pass |
| Comp. Example 3 | 0.6 | 0.5 | 1.2 | 1.3 | 3.0 | Fail |
| Comp. Example 4 | 1.9 | 4.9 | 4.9 | 2.9 | 3.0 | Fail |
| Comp. Example 5 | 3.5 | 0.9 | 4.3 | 4.3 | 3.3 | Fail |
| Comp. Example 6 | 2.9 | 3.5 | 4.9 | 4.3 | 4.3 | Pass |
| Comp. Example 7 | 4.9 | 4.9 | 4.9 | 4.3 | 3.2 | Pass |
| Comp. Example 8 | 3.6 | 3.5 | 3.4 | −0.1 | −0.2 | Fail |
| Comp. Example 9 | 4.9 | 4.9 | 4.9 | 2.0 | 2.0 | Pass |

As shown in Tables 1 and 2, Examples 1-4 do not contain surfactants to stabilize the preservative system, yet each variable still received an overall MST score of "Pass". Comparative Examples 3-5 and 8 each received an overall MST score of "Fail". Comparative Examples 1, 2, 7, and 9 received an overall MST score of "Pass", however, each required at least one surfactant in order to stabilize the preservative system. Comparative Example 6, which received an overall MST score of "Pass", contains the chelator tetrasodium glutamate diacetate, which may be perceived by consumers as a harsh chemical that may not be suitable for some applications, such as baby wipes.

Table 3 shows the results of the Benzoate Retention Test on samples comprising different substrate materials, as measured by the Benzoate Retention Test Method Example 5: The wet wipe of the present disclosure described as Example 5 is a substrate comprising a 50:50 blend of viscose and lyocell in a lotion comprising 98.06% water, 0.18% sodium benzoate, 0.56% citric acid (50% solution), 0.30% sodium citrate, 0.44% PEG-40 HCO, 0.2% sorbitan caprylate, 0.1% disodium EDTA, 0.1% silicon-based nonionic emulsifier, and 0.06% perfume. The lotion load rate is 390% by weight of the substrate.

Example 6: The wet wipe of the present disclosure described as Example 6 is a substrate comprising a blend of 40% TPP fibers, 40% PET fibers, and 20% viscose fibers lyocell in a lotion comprising 98.06% water, 0.18% sodium benzoate, 0.56% citric acid (50% solution), 0.30% sodium citrate, 0.44% PEG-40 HCO, 0.2% sorbitan caprylate, 0.1% disodium EDTA, 0.1% silicon-based nonionic emulsifier, and 0.06% perfume. The lotion load rate is 390% by weight of the substrate.

Example 7: The wet wipe of the present disclosure described as Example 7 is a substrate comprising a blend of 70% PET fibers, 15% cotton fibers, and 15% viscose lyocell in a lotion comprising 98.06% water, 0.18% sodium benzoate, 0.56% citric acid (50% solution), 0.30% sodium citrate, 0.44% PEG-40 HCO, 0.2% sorbitan caprylate, 0.1% disodium EDTA, 0.1% silicon-based nonionic emulsifier, and 0.06% perfume. The lotion load rate is 390% by weight of the substrate.

Comparative Example 10: The wet wipe of the present disclosure described as Comparative Example 10 is a substrate comprising a blend of 80% PET fibers and 20% viscose fibers in a lotion comprising 98.06% water, 0.18% sodium benzoate, 0.56% citric acid (50% solution), 0.30% sodium citrate, 0.44% PEG-40 HCO, 0.2% sorbitan caprylate, 0.1% disodium EDTA, 0.1% silicon-based nonionic emulsifier, and 0.06% perfume. The lotion load rate is 390% by weight of the substrate.

TABLE 3

|  |  | Benzoate retention in lotion over time reported as % of initial fortification (Benzoate Retention Factor) | | | |
|---|---|---|---|---|---|
|  | Substrate Material | ~5 Days | 1 Month | 2 Months | 3 Months |
| Example 5 | 50% Viscose, 50% Lyocell | 85.1 | 76.6 | — | 72.6 |
| Example 6 | 40% TPP, 40% PET, 20% Viscose | 77.2 | 54.2 | — | 51.7 |
| Example 7 | 70% PET, 15% Cotton, 15% Viscose | 67.6 | 60.7 | 67.4 | — |
| Comp. Example 10 | 80% PET, 20% Viscose | 50.6 | 25.6 | — | 21.7 |

As shown in Table 3, Examples 5-7, each comprising at least 30% cellulosic fiber material, retains more benzoate in the lotion over time as compared to Comparative Example 10, which comprises less than 30% cellulosic fiber material.

Table 4 shows data from a comparison of Bacterial Log Reduction Values, Yeast and Mold Log Reduction Values, and Overall MST Scores between high PET and low PET substrates.

Examples 1-4 are described above.

Comparative Example 11: The wet wipe of the present disclosure described as Comparative Example 11 is a substrate comprising an 80:20 blend of PET and viscose in a lotion comprising 98.22% water, 0.2% sodium benzoate, 0.3% succinic acid, 0.88% citric acid (50% solution), 0.30% sodium citrate, and 0.10% phytic acid. The lotion load rate is 390% by weight of the substrate.

Comparative Example 12: The wet wipe of the present disclosure described as Comparative Example 12 is a substrate comprising an 80:20 blend of PET and viscose in a lotion comprising 98.22% water, 0.2% sodium benzoate, 0.3% succinic acid, 0.88% citric acid (50% solution), 0.30% sodium citrate, and 0.10% sodium phytate. The lotion load rate is 390% by weight of the substrate.

TABLE 4

|  | Bacteria Log Reduction Value (log reduction) | | | Yeast & Mold Log Reduction Value (log reduction) | | Overall MST Score |
|---|---|---|---|---|---|---|
|  | Day 2 | Day 7 | Day 28 | Day 14 | Day 28 | (pass/fail) |
| Example 1 | 4.4 | 5.2 | 5.2 | 4.2 | 4.7 | Pass |
| Example 2 | 5.2 | 5.2 | 5.2 | 4.0 | 4.7 | Pass |
| Example 3 | 5.2 | 5.2 | 5.2 | 4.7 | 4.7 | Pass |

TABLE 4-continued

|  | Bacteria Log Reduction Value (log reduction) | | | Yeast & Mold Log Reduction Value (log reduction) | | Overall MST Score |
| --- | --- | --- | --- | --- | --- | --- |
|  | Day 2 | Day 7 | Day 28 | Day 14 | Day 28 | (pass/fail) |
| Example 4 | 5.2 | 5.2 | 5.2 | 4.7 | 4.7 | Pass |
| Comp. Example 11 | 3.8 | 3.4 | 1.8 | 2.2 | 1.3 | Fail |
| Comp. Example 12 | 2.3 | 5.2 | 5.2 | 2.2 | 4.7 | Pass |

Comparison of MST Reduction Value between high PET and low PET substrates.

As shown in Table 4, Examples 1-4, in which the substrate comprises greater than 30% cellulosic fibers, each received an MST score of "Pass". Examples 1 and 3 each comprise phytic acid as a component of the preservative system, whereas Examples 2 and 4 each comprise sodium phytate. Thus, phytate is shown to be an effective component of the preservative system (see Table 1), and phytate may be incorporated into a lotion as phytic acid and/or a salt thereof. Furthermore, Examples 1 and 2 both have a reduced lotion loading rate of 325%, as compared to 390% in Examples 3 and 4. Thus, the lotion may be effective even at a reduced loading rate.

Comparative Example 11, which comprises a substrate comprising 80% PET, received an MST score of "Fail". Without wishing to be bound by theory, it is believed that the PET of the substrate interacts with the benzoate in the lotion, prohibiting the benzoate from participating in the preservative system and reducing the ability of the lotion to reduce and/or inhibit microbial growth. Similarly, Comparative Example 12, while receiving an MST score of "Pass", showed reduced efficacy of the of the preservative system, especially at early timepoints. It is believed that the high level of PET in the substrate of Comparative Example 12 inhibited the preservative system by removing benzoate from the lotion preservative system.

Aspects

The following aspects are provided as examples in accordance with the disclosure herein and are not intended to limit the scope of the disclosure.

1. A wet wipe comprising:
    a substrate comprising cellulosic fibers; and
    a lotion comprising:
       between about 96.0% and about 99.5%, by weight of the lotion, of water;
       a pH buffering system; and
       a preservative system comprising:
          benzoic acid and/or a salt thereof,
          succinic acid and/or a salt thereof, and
          phytic acid and/or a salt thereof;
    wherein the lotion has a pH of about 3.5 to about 5.
2. The wet wipe of paragraph 1, wherein the substrate comprises between about 30% to about 100%, by weight of the substrate, of cellulosic fibers.
3. The wet wipe of any one of the preceding paragraphs, wherein the substrate is free of polyesters, polyamides, and/or polyolefins.
4. The wet wipe of any one of the preceding paragraphs, wherein the substrate comprises cotton fibers.
5. The wet wipe of any one of the preceding paragraphs, wherein the substrate comprises regenerated cellulose fibers.
6. The wet wipe of paragraph 5, wherein the substrate comprises lyocell fibers.
7. The wet wipe of paragraph 5, wherein the substrate comprises viscose fibers.
8. The wet wipe of paragraph 7, wherein at least a portion of the viscose fibers are tri-lobal.
9. The wet wipe of paragraph 7, wherein at least a portion of the viscose fibers are circular in cross-section.
10. The wet wipe of any one of the preceding paragraphs, wherein the lotion is devoid of fatty acid-containing materials.
11. The wet wipe of any one of the preceding paragraphs, wherein the lotion is devoid of surfactants.
12. The wet wipe of any one of the preceding paragraphs, having a Benzoate Retention Factor at 1 month of between about 45% and about 99%, according to the Benzoate Retention Test Method.
13. The wet wipe of any one of the preceding paragraphs, wherein the pH buffering system comprises citric acid and/or a salt thereof.
14. The wet wipe of any one of the preceding paragraphs, wherein the lotion has a Bacterial Log Reduction Factor of greater than or equal to 3 at day 28, according to the Microbiological Susceptibility Test Method.
15. The wet wipe of any one of the preceding paragraphs, wherein the lotion has a Yeast and Mold Log Reduction Factor of greater than or equal to 2 at day 28, according to the Microbiological Susceptibility Test Method.
16. A wet wipe comprising:
    a substrate comprising 100% cellulosic fibers, and
    a lotion comprising:
       between about 96.0% and about 99.5%, by weight of the lotion, of water;
       a pH buffering system; and
       a preservative system comprising:
          benzoic acid and/or a salt thereof;
          succinic acid and/or a salt thereof; and
          phytic acid and/or a salt thereof;
    wherein the lotion has a pH of about 3.5 to about 5.
17. The wet wipe of paragraph 16, wherein the substrate comprises between about 30% and about 90%, by weight of the substrate, of lyocell.
18. The wet wipe of paragraph 16 or 17, wherein the substrate comprises between about 10% and about 70%, by weight of the substrate, of viscose fibers.
19. The wet wipe of paragraph 18, wherein at least a portion of the viscose fibers are trilobal.
20. The wet wipe of paragraph 18 or 19, wherein at least a portion of the viscose fibers are round.
21. The wet wipe of any one of paragraphs 16-20, wherein the substrate comprises cotton.
22. The wet wipe of any one of paragraphs 16-21, wherein the lotion is devoid of fatty acid-containing materials.
23. The wet wipe of any one of paragraphs 16-22, wherein the lotion is devoid of surfactants.
24. The wet wipe of any one of paragraphs 16-23, having a Benzoate Retention Factor at 3 months of between about 40% and about 99%, according to the Benzoate Retention Test Method.
25. The wet wipe of any one of paragraphs 16-24, wherein the lotion has a Bacterial Log Reduction Factor of greater than or equal to 3 at day 28, according to the Microbiological Susceptibility Test Method.
26. The wet wipe of any one of paragraphs 16-25, wherein the lotion has a Yeast and Mold Log Reduction Factor of greater than or equal to 2 at day 28, according to the Microbiological Susceptibility Test Method.

27. The wet wipe of any one of paragraphs 16-26, wherein the preservative system consists of natural compounds.
28. A wet wipe comprising:
a substrate comprising 100% cellulosic fibers, and
a lotion comprising:
between about 96.0% and about 99.5%, by weight of the lotion, of water;
a pH buffering system; and
a preservative system comprising:
benzoic acid and/or a salt thereof;
succinic acid and/or a salt thereof; and
phytic acid and/or a salt thereof;
wherein the lotion is devoid of fatty acid-containing materials;
wherein the wet wipe has a benzoate retention factor at 1 month of between about 45% and about 99%, according to the Benzoate Retention Test Method;
wherein the lotion has a Bacterial Log Reduction Factor of greater than or equal to 3 at day 28, according to the Microbiological Susceptibility Test Method;
wherein the lotion has a Yeast and Mold Log Reduction Factor of greater than or equal to 2 at day 28, according to the Microbiological Susceptibility Test Method; and
wherein the lotion has a pH of about 3.6 to about 4.4.
29. The wet wipe of any one of paragraphs 1, 16, and 20, wherein the substrate consists of cellulosic fibers.
30. The wet wipes of any one of paragraphs 1, 16, and 20, wherein the substrate consists of cotton fibers.

Test Methods

All test methods are carried out in an environment 23±2° C. and 50±5% relative humidity environment, unless otherwise specified.

Lotion Expression Method

Lotion is expressed from wet wipes for further analysis using the Lotion Expression Method. In this method, lotion is extracted from one or more like packages of lotioned wipes that have been wetted in a sealed package for at least 28 days at 40° C. and 75% relative humidity in order to collect a desired quantity of lotion for further analysis.

One corner is cut from one sealed wipes package to create a small (approximately 0.25-inch in diameter) hole from which liquid can escape. The package is then positioned between the platens of a uniaxial press with the corner containing the hole for liquid escape hanging outside the edge of the platens such that lotion can be collected in a suitable container as pressure is applied. Pressure is then increasingly applied to the package of wipes and held at 100±10 psi for at least one minute and until no more fluid drains freely from the compressed lotion package, at which point the container holding the collected lotion is sealed tightly until further analysis. This process is repeated until the desired quantity of lotion for further analysis has been collected. If lotion is collected from more than one package of like wipes, all lotion expressed from all like packages is mixed prior to any analysis.

If lotioned wipes are packaged directly in packaging that is not amenable to the pressure/deformation required by this method, lotioned wipes are removed from packaging and are immediately transferred to a clean rectangular plastic bag and sealed. The rectangular plastic bag is then cut at one corner and placed in the platens of a press and squeezed as specified above.

Water Content Test Method

In the Water Content Test Method, a portion of expressed lotion is placed in an oven to facilitate evaporation, and the remaining unevaporated mass is measured. From this, the water content of the starting expressed lotion is calculated.

The Lotion Expression Method is used to express lotion, from which a 5.0±0.1 g aliquot is taken and placed in a 70-mm diameter aluminum weighing boat (such as VWR part number 25433-089, VWR International, Radmor, PA, USA, or equivalent), and the initial mass of the lotion aliquot is determined to at least the nearest 0.001 g. Immediately following weighing, the weighing boat containing the lotion is placed in an oven held at 100° C. for 12±1 hour, at which point the boat containing the unevaporated material remaining from the aliquot is removed, and the mass of unevaporated material is determined to the nearest 0.001 g. The quotient of the unevaporated mass remaining from the lotion aliquot to the initial mass of the lotion aliquot, expressed as a percent to the nearest tenth of a percent, is defined as the Lotion Percent Solids Parameter. The Lotion Percent Solids Parameter is subtracted from 100.0%, and the resulting difference is defined as the Lotion Percent Water Parameter.

Buffering Capacity Test Method

In the Buffering Capacity Test Method, the mass of base solution required to bring a specified mass of lotion to a characteristic equivalence point is measured and expressed as a ratio of mass of added base to initial mass of lotion, and this dimensionless ratio is defined as the Equivalence Value.

The Lotion Expression Method is used to express 40.0±0.1 g of lotion. The pH of the lotion is measured to the nearest 0.01 unit of pH with a pH meter. If the pH of the lotion is equal to or greater than 10.00, the Equivalence Value is defined as 0. Otherwise, 0.1 N sodium hydroxide is added to the initial 40.0±0.1 g of expressed lotion with stirring and pH is measured and recorded as a function of added volume of base to the nearest 0.01 until the pH reaches 10.00. The pH versus mass 0.1 N sodium hydroxide added data are then examined, and the mass of added base at which the rate of change of pH with respect to addition of base is at a maximum is found and recorded in grams to the nearest 0.01 g as the Equivalence Mass. The Equivalence Mass divided by the initial mass of expressed lotion (40.0±0.1 g), then multiplied by 100, is defined as the Equivalence Value, reported to the hundredths place in dimensionless units.

Benzoate Retention Test Method

The Benzoate Retention Test Method is used to determine the Benzoate Retention Factor, which is the weight percent of the total benzoate species (benzoic acid and the corresponding deprotonated conjugate base benzoate ion) in the wet wipe lotion composition. The Benzoate Retention Factor is determined using High Pressure Liquid Chromatography (HPLC) as follows.

In this method, HPLC performed using a mobile phase at a pH of approximately 2 is used to determine the content of total benzoate species of expressed wet wipe lotion. Here, total benzoate species refers to the presence of both benzoic acid and its conjugate base benzoate ion. The use of a mobile phase with a pH (pH approx. 2) significantly below the pKa of benzoic acid (pKa=4.2) results in essentially all benzoate species being in the form of benzoic acid, which is directly measured via HPLC separation and detection. The HPLC result can then be used together with the measured pH of expressed lotion to calculate the content of benzoic acid in the expressed lotion.

An HPLC instrument (such as Waters 2695, Waters Corporation, Milford, MA, USA, or equivalent) is configured for isocratic separation with a flow rate of 1.5 mL/min, an injection volume of 10 µL, a column temperature of 35±1° C., and UV detection at a wavelength of 254 nm. An octadecyl reversed-phase silica column, 4.6×100 mm, particle size 3 or 3.5 µm, (such as Waters SunFire C18, part number #186002553, or equivalent) is used. A guard column (such as Phenomenex SecurityGuard Cartridges C18 4×2 mm, part number #AJ0-4286, Phenomenex Inc., Torrence, CA, USA, or equivalent) is recommended.

A phosphoric acid buffer mobile phase solution is prepared by adding 3.8±0.1 g of monosodium phosphate and 3.2±0.1 g of 85-90% phosphoric acid to 1300 mL of HPLC grade water and 325 mL of acetonitrile. Five standard solutions of benzoic acid are prepared using the mobile phase solution using class A volumetric pipettes and flasks with levels (precisely known) of approximately 20, 40, 100, 200, and 300 µg/mL.

The Lotion Expression Method is used to express all lotion from one package of wipes. (If this lotion is less than 50 mL in volume, the Lotion Expression Method is used to express lotion from additional like packages of wipes until the volume of expressed lotion exceeds 50 mL.) The pH of the quantity of lotion expressed is measured and recorded to the nearest 0.01 unit of pH. From the quantity of lotion expressed is weighed a sample 5.0±0.1 g (mass recorded to the nearest 0.1 mg), which is added to a 50 mL volumetric flask and diluted to volume with mobile phase. The ratio of sample mass to dilution volume, expressed in units of µg/mL, is defined as the dilution factor. This resulting solution is referred to as the sample as prepared. (If, after injection of standards and sample as prepared, it is found that the benzoic acid content of the sample as prepared lies outside the range of standards, another sample is prepared as above but adjusting the dilution such that the benzoic acid content lies within the range of benzoic acid standards, and a revised dilution factor is recorded.)

All five standards and the prepared sample are injected sequentially into the HPLC instrument. (Given the separation conditions specified, the benzoic acid peak generally occurs at around 5.5 minutes of elution time, but its exact position is confirmed via position in the standards.) A calibration curve of benzoic acid peak area versus benzoic acid concentration is fitted linearly to the peak areas of the five standards, and this linear fit is used to calculate the concentration (in µg/mL) benzoic acid in the sample as prepared, and this value is recorded to the nearest 0.1 µg/mL. The concentration of benzoic acid in the sample as prepared is then multiplied 100% and divided by the dilution factor to arrive at the weight percent of total benzoate species in the expressed lotion.

The weight percent of total benzoate species in the expressed lotion of each sample is divided by the initial fortification rate (projected or tested) of total benzoate species for the variable. The Benzoate Retention Factor is found by the following equation:

$$\text{Bensoate Retention Factor} = \frac{Wt.\% \text{ of total benzoate sepcies in sample}}{Wt.\% \text{ of initial benzoate species fortification}} * 100$$

The Benzoate Retention Factor may be determined on variables of wet wipe products at various intervals over the shelf life of the wet wipe product.

Microbiological Susceptibility Test (MST) Method

The Microbiological Susceptibility Test Method is used to determine the MST Bacteria Reduction Value, Yeast & Mold MST Reduction Value, and to assign an overall MST pass/fail score to wet wipes. The Microbiological Susceptibility Test Method follows the United States Pharmacopoeia ⟨51⟩ Antimicrobial Effectiveness Test. The inoculation procedure is modified for application to wetted wipes as follows.

For each sample prepared, an entire previously sealed, unopened package of wetted wipes is opened, and 10.0±1.0 g of wipes is removed from as closely as possible to the middle of the stack of wipes and is aseptically weighed into a sterile container. Wipes are cut, if needed, in order for the sample to meet the mass target. Inoculum consists of *Candida albicans, Aspergillus brasiliensis* (Yeast/Mold pool), *Staphylococcus aureus, Pseudomonas aeruginosa, Escherichia coli, Burkholderia cepacia, Klebsiella pneumoniae, Enterobacter gergoviae*, and *Serratia marcescens* (Bacterial pool). Prior to inoculation, each mixed inoculum is further diluted from the recommended level 1:10 in sterile 0.85% NaCl (w/w) saline solution. 1.0±0.1 mL of this resulting diluted inoculum is then spread as uniformly as is feasible across the wipes sample. Inoculated samples are stored at 22.5±2.5° C. until sampling. At the time of sampling, each wipes sample is added to 90 mL of liquid growth medium and is homogenized for two minutes at 260 RPM using a stomacher (such as the Stomacher 400 Circulator, Seward Ltd., West Sussex, UK, or equivalent). Additional 1:10 dilutions are performed using liquid growth medium (to achieve 1:100, 1:1000 dilutions and so on) as needed to enable a meaningful plate count. Plate counts are performed on 100-mm diameter petri plates, and ideal CFU readings for plates are between 25 and 250 for bacteria and yeasts, and between 8 and 80 for mold. For each microorganism, the lowest dilution factor that leads to a raw CFU reading that falls within the allowed range is ideally used to calculate CFU/mL of survivors.

Using the determined starting and surviving concentration of each microorganism (at day 2, day 7, and day 28 for bacteria, and at day 14 and day 28 for yeast and old), as determined by USP ⟨51⟩, the Bacterial Log Reduction Value and Yeast and Mold Log Reduction Value are calculated.

The Starting Pooled Bacteria Concentration is defined as the sum of starting concentrations (in CFU/mL) for each of the bacterial microorganisms analyzed. The Pooled Bacteria Concentration is the sum of measured concentrations (in CFU/mL) of survivors for each bacterium analyzed at a given day X (day 2, day 7, and day 28). The ratio of the Pooled Bacteria Concentration at X Days versus the Starting Pooled Bacteria Concentration is used to calculate the Bacterial Log Reduction Value.

$$\text{Bacterial Log Reduction Value} = -\log_{10} \frac{\text{Pooled Bacteria Concentration at } X \text{ Days}}{\text{Starting Pooled Bacteria Concentration}}$$

The Bacterial Log Reduction Value is reported to the nearest tenth of a log unit.

The Starting Pooled Yeast and Mold Concentration is defined as the sum of starting concentrations (in CFU/mL) for each of the yeast and mold microorganisms analyzed. The Pooled Yeast and Mold Concentration is the sum of measured concentrations (in CFU/mL) of survivors for each yeast and mold analyzed at a given day X (day 14 and day 28). The ratio of the Pooled Yeast and Mold Concentration at X Days versus the Starting Pooled Yeast and Mold Concentration is used to calculate the Yeast and Mold Log Reduction Value.

$$\text{Yeast and Mold Log Reduction Value} = -\log_{10} \frac{\text{Pooled Yeast and Mold Concentration at 28 Days}}{\text{Starting Pooled Yeast and Mold Concentration}}$$

The Yeast and Mold Log Reduction Value is reported to the nearest tenth of a log unit.

The overall MST Pass/Fail score is determined using the success criteria in Table 5 below. A sample receives a "Pass" score when it meets or exceeds the success criteria and receives a "Fail" score when it falls below the success criteria.

TABLE 5

|  | Day 2 | Day 7 | Day 14 | Day 28 |
|---|---|---|---|---|
| Bacteria | ≥2 log Reduction Value | ≥3 log Reduction Value | None | No increase from Day 7 |
| Mold/Yeast | None | None | ≥2 log Reduction Value | No increase from day 14 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of this present disclosure.

What is claimed is:

1. A wet wipe comprising:
   a substrate comprising cellulosic fibers; and
   a lotion comprising:
      between about 96.0% and about 99.5%, by weight of the lotion, of water;
      a pH buffering system; and
      a preservative system comprising:
         benzoic acid and/or a salt thereof,
         succinic acid and/or a salt thereof, and
         phytic acid and/or a salt thereof;
   wherein the lotion has a pH of about 3.5 to about 5; and
   wherein the lotion is devoid of fatty acid-containing materials.

2. The wet wipe of claim 1, wherein the substrate comprises between about 30% to about 100%, by weight of the substrate, of cellulosic fibers.

3. The wet wipe of claim 1, wherein the substrate is free of polyesters, polyamides, and/or polyolefins.

4. The wet wipe of claim 1, wherein the substrate comprises cotton fibers.

5. The wet wipe of claim 1, wherein the substrate comprises regenerated cellulose fibers.

6. The wet wipe of claim 5, wherein the substrate comprises lyocell fibers.

7. The wet wipe of claim 5, wherein the substrate comprises viscose fibers.

8. The wet wipe of claim 7, wherein at least a portion of the viscose fibers are tri-lobal.

9. The wet wipe of claim 7, wherein at least a portion of the viscose fibers are circular in cross-section.

10. The wet wipe of claim 1, wherein the lotion is devoid of surfactants.

11. The wet wipe of claim 1, having a Benzoate Retention Factor at 1 month of between about 45% and about 99%, according to the Benzoate Retention Test Method.

12. The wet wipe of claim 1, wherein the pH buffering system comprises citric acid and/or a salt thereof.

13. The wet wipe of claim 1, wherein the lotion has a Bacterial Log Reduction Factor of greater than or equal to 3 at day 28, according to the Microbiological Susceptibility Test Method.

14. The wet wipe of claim 1, wherein the lotion has a Yeast and Mold Log Reduction Factor of greater than or equal to 2 at day 28, according to the Microbiological Susceptibility Test Method.

15. A wet wipe comprising:
   a substrate comprising 100% cellulosic fibers, and
   a lotion comprising:
      between about 96.0% and about 99.5%, by weight of the lotion, of water;
      a pH buffering system; and
      a preservative system comprising:
         benzoic acid and/or a salt thereof;
         succinic acid and/or a salt thereof; and
         phytic acid and/or a salt thereof;
   wherein the lotion has a pH of about 3.5 to about 5; and
   wherein the lotion is devoid of fatty acid-containing materials.

16. The wet wipe of claim 15, wherein the substrate comprises between about 30% and about 90%, by weight of the substrate, of lyocell.

17. The wet wipe of claim 15, wherein the substrate comprises between about 10% and about 70%, by weight of the substrate, of viscose fibers.

18. The wet wipe of claim 15, wherein the substrate comprises cotton.

19. The wet wipe of claim 15, wherein the lotion is devoid of surfactants.

20. The wet wipe of claim 1, wherein the lotion consists of:
   water,
   benzoic acid and/or a salt thereof,
   succinic acid and/or a salt thereof, and
   phytic acid and/or a salt thereof;
   citric acid; and
   sodium citrate.

\* \* \* \* \*